(12) United States Patent
Ellman et al.

(10) Patent No.: US 6,293,944 B1
(45) Date of Patent: Sep. 25, 2001

(54) COMBINED SYRINGE AND ELECTROSURGICAL ELECTRODE FOR SCLEROTHERAPY

(76) Inventors: Alan G. Ellman; Jon C. Garito, both of 1135 Railroad Ave., Hewlett, NY (US) 11557

( * ) Notice: Subject to any disclaimer, the term of this patent is extended or adjusted under 35 U.S.C. 154(b) by 0 days.

(21) Appl. No.: 09/393,285

(22) Filed: Sep. 10, 1999

(51) Int. Cl.[7] .................................................. A61B 18/18
(52) U.S. Cl. ................................ 606/41; 606/49; 128/898
(58) Field of Search ................................ 606/27–31, 41, 606/44, 48–50; 128/898

(56) References Cited

U.S. PATENT DOCUMENTS

| | | | |
|---|---|---|---|
| 3,301,258 | * | 1/1967 | Werner et al. ........................ 606/29 |
| 4,269,174 | * | 5/1981 | Adair ................................... 606/49 |
| 4,483,338 | * | 11/1984 | Bloom et al. ......................... 606/49 |
| 4,920,982 | * | 5/1990 | Goldstein .............................. 606/29 |
| 5,336,222 | * | 8/1994 | Durgin, Jr. et al. .................. 606/50 |
| 5,403,311 | * | 4/1995 | Abele et al. ........................... 606/49 |
| 5,437,664 | * | 8/1995 | Cohen et al. ......................... 606/42 |

* cited by examiner

*Primary Examiner*—Michael Peffley

(57) ABSTRACT

A hypodermic needle syringe with means connected to the needle for selectively applying to the needle radio-frequency (RF) electrosurgical currents. For treating varicose veins, the hypodermic needle is inserted into the vein to be treated and the syringe plunger withdrawn to see whether blood is back drawn into the syringe barrel. If blood is detected, then the electrosurgical apparatus is activated and the resultant application of the RF electrosurgical currents quickly collapses the vein. An advantage is that the needle need not be withdrawn after the blood is detected, with the result that no problem arises of trying to locate a pin hole previously produced by a needle.

6 Claims, 3 Drawing Sheets

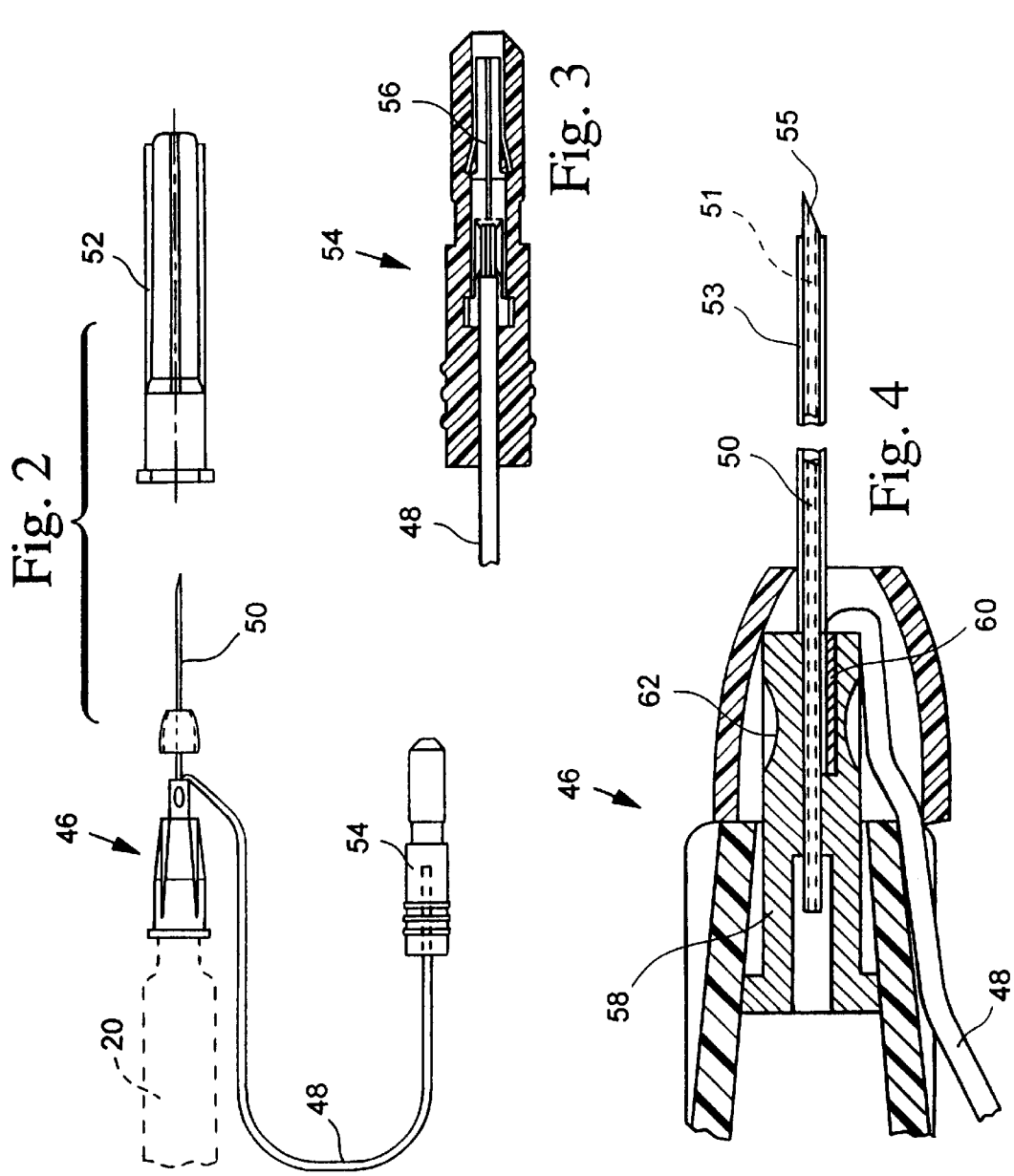

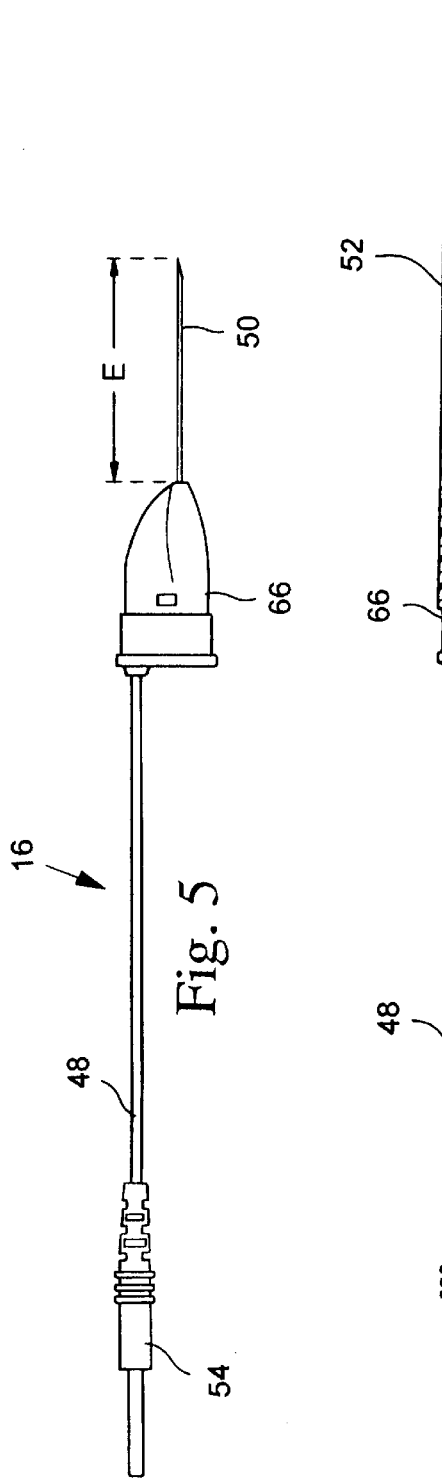
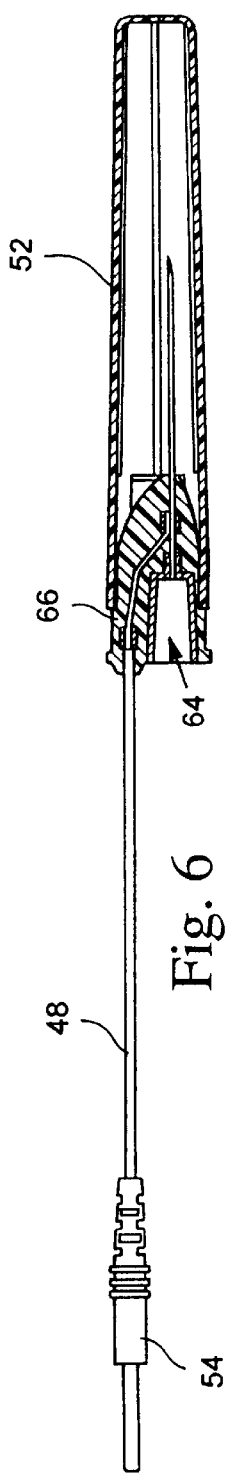
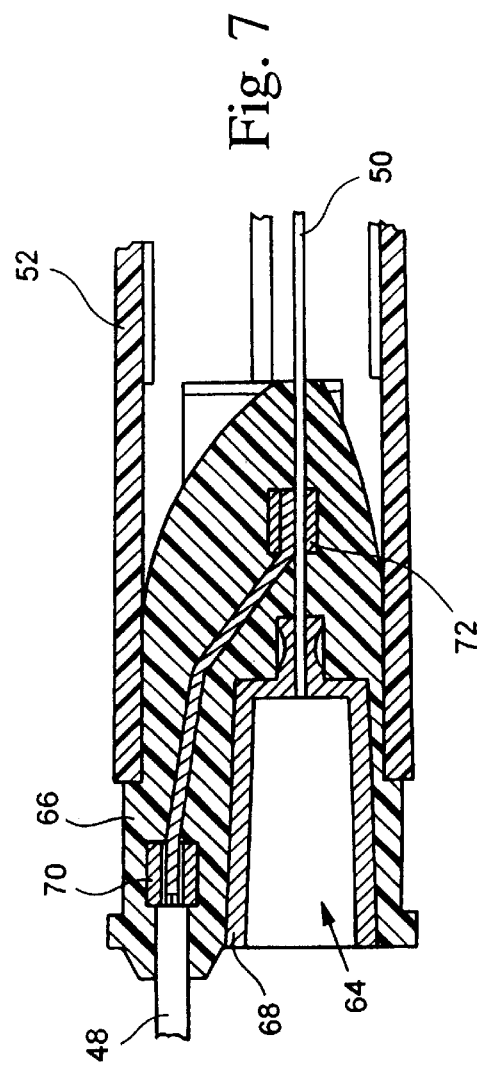

US 6,293,944 B1

COMBINED SYRINGE AND ELECTROSURGICAL ELECTRODE FOR SCLEROTHERAPY

This invention relates to an electrosurgical electrode for electrosurgical scierotherapy, i.e., the treatment of varicose veins of a patient.

BACKGROUND OF THE INVENTION

Reference is made to our U.S. Pat. No. 5,695,495, whose contents are herein incorporated by reference, which describes an electrosurgical electrode for scierotherapy. The latter replaces an earlier form of sclerotherapy which involves introducing a sclerosing agent, be it physical, chemical or mechanical, into a vessel to produce sclerosis. The advantage of our patented electrosurgical electrode is that it enables physicians to offer to patients a treatment that is virtually non-invasive and non-surgical, efficiently performed, easily learned by the physician and thus performed at a significantly reduced price, and requiring less patient follow-up with superior results compared to non-electrosurgical procedures.

The common manner to implement this new procedure and in a sense a possible disadvantage is that the precise vein to be treated is first identified by placing the hollow needle of a hypodermic syringe into the skin/vein interface, and withdrawing the plunger. If blood is back drained into the syringe barrel, then the practitioner by viewing the blood knows the syringe needle is in the vein to be treated. Once the vein is thus identified, the needle is removed and the patented insulated needle electrode is placed carefully trying to locate the same needle or hole site formed by the syringe needle as well as depth location of where the vein was. This can be a difficult and tedious task and often results in losing the previously identified vein. The procedure then has to be repeated. The time necessary to find the correct vein can be consuming.

SUMMARY OF THE INVENTION

An object of the invention is an improved surgical procedure for the treatment of varicose veins.

Another object of the invention is an improved instrument for the electrosurgical treatment of varicose veins.

A further object of the invention is an improved electrosurgical instrument to accomplish the end result of collapsing the offending varicose vein.

We have invented a novel instrument for use in electrosurgical scierotherapy. Essentially, the new instrument combines a hypodermic needle syringe with means connected to the needle for selectively applying to the needle radiofrequency (RF) electrosurgical currents. In operation, the hypodermic needle is inserted into the vein to be treated and the plunger withdrawn to see whether blood is back drawn into the syringe barrel. If blood is detected, then the practitioner simply activates the electrosurgical apparatus and the resultant application of the RF electrosurgical currents quickly collapses the vein. As will be evident, the needle need not be withdrawn after the blood is detected, with the result that no problem arises of trying to locate a pin hole previously produced by a needle.

It will be noted that FIG. 4 of the referenced patent describes an embodiment in which the needle used was a cannula. However, the specification makes clear that the needle bore is not used in the sclerotherapy described in the patent. At the time that the patent specification was drafted and while it was prosecuted, it never occurred to us to attach a syringe to the needle for any purpose. In fact, using either the embodiment of a solid needle or a hollow needle for attachment to a conventional electrosurgical handpiece made it impossible to attach a hypodermic syringe to the needle. The needle with the cannula was only mentioned as it seemed at the time that such needles might be more readily purchased than a solid needle. It wasn't until after the referenced patent was issued that the problems associated with its use came to our attention and triggered this invention.

As is described in the issued patent, the needle part of our electrosurgical syringe, except for the tip which is inserted into the vein to be treated, is insulated to prevent undesired electrical discharges to tissue surrounding the vein to be treated.

The procedure using our novel syringe electrode is based on superficial damage or destruction of the tissues lining the wall of the vein, causing collapse and obstruction of the vein. The electrode of the invention is configured to enable the active tip to reach and electrosurgically damage or destroy the vein lining with minimal damage to the surrounding tissue. The needle electrode is moved through the vein while it remains energized and then removed to determine whether the desired effect has been realized or a retreatment may be necessary during the same patient visit.

In a preferred embodiment, the needle part of our novel electrode is characterized by a bare active sharpened tip of a fine needle whose portions extending beyond the exposed tip are completely insulated by a thin electrically-insulating coating. A family of needle electrodes can be provided of increasing gauges to fit easily within large, medium, or small varices. Some medial and lateral fanning of the active point may be desirable while moving the needle, including preferably withdrawing the needle, to contact as much of the tissue lining the veins being treated as possible. The portions of the needle adjacent to the tip are made insulating to avoid excessive heating and to concentrate the high frequency currents at the needle tip. The electrosurgical procedure using the needle electrode has the important advantages of concentrating the currents causing the tissue damage at the tissue required, with minimal damage to surrounding tissue, in a relatively fast procedure, and with little pain or trauma for the patient.

It is preferred that the electrosurgical currents used be above 2 MHz, and preferably above 3 MHz. At these high frequencies, commonly referred to as radiosurgery, destruction is accomplished by volatilizing intracellular fluids at the point of the transmitting electrode contact which is primarily responsible for only small lateral heat spread and thus less damage to neighboring cell layers.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

BRIEF DESCRIPTION OF THE DRAWINGS

In the drawings:

FIG. 2 is an exploded view of another form of the combined electrosurgical needle syringe of the invention;

FIG. 3 is a partial cross-sectional view of the cable connector of the FIG. 2 embodiment;

FIG. 4 is an enlarged partial cross-sectional view of the needle holder of the FIG. 2 embodiment;

FIG. 5 is a side view of the combined electrosurgical needle syringe in accordance with the invention illustrated in FIG. 1;

FIG. 6 is a partial cross-sectional view of the needle syringe of FIG. 5;

FIG. 7 is an enlarged partial cross-sectional view of the needle holder of the FIG. 5 embodiment.

DETAILED DESCRIPTION OF THE PREFERRED EMBODIMENTS

Figure 1:
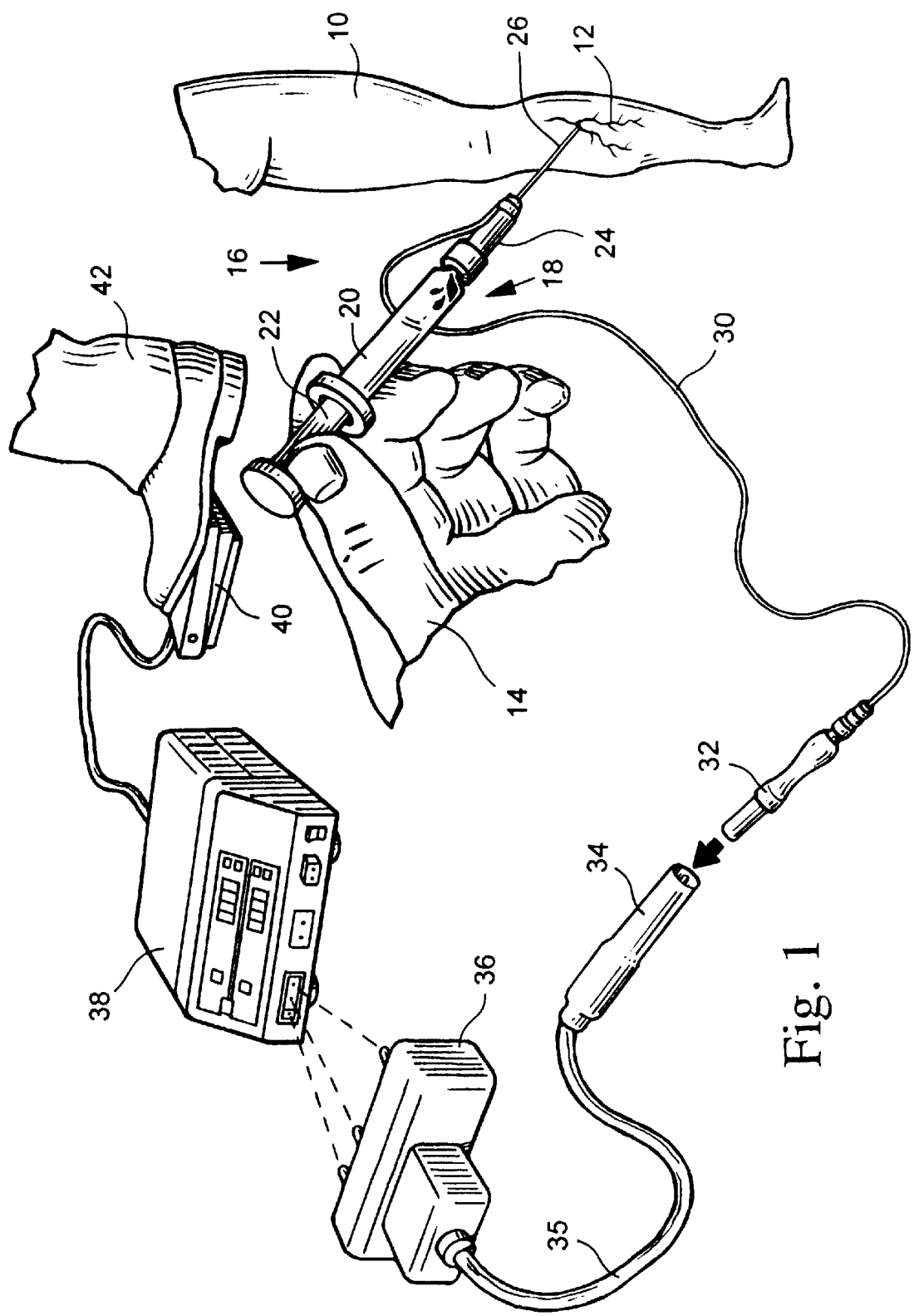
FIG. 1 is a schematic view illustrating treatment of a patient with one form of the combined electrosurgical needle syringe of the invention.

In the schematic view of FIG. 1, 10 represents the leg of a patient having varicose veins 12 to be treated. The hand 14 of the practitioner holds one form 16 of the combined electrosurgical needle syringe of the invention. It comprises a syringe 18 having a barrel 20 with a conventional plunger 22 to the end of which is attached a needle holder or hub as it is sometimes called 24 for a hypodermic needle 26, to which needle is electrically connected a cable 30 which terminates in a male cable connector 32 which can be plugged into a female cable connector 34 in turn connected via a cable 35 to an adaptor 36 of the type described in our U.S. Pat. No. 4,463,759, whose contents are herein incorporated by reference. The adaptor 36 in turn is plugged into a conventional electrosurgical apparatus 38 (See Design Pat. No. 396,108) which can be activated, for example, by a foot switch 40 operated by the practitioner's foot 42.

The embodiment illustrated in FIG. 1 is described in detail in FIGS. 5–7, which will be better understood by first describing another embodiment of the invention in connection with FIGS. 2–4. In the FIG. 2 embodiment, the syring barrel is shown in dashed lines at 20, to which is attached, usually by a friction fit, a hub or needle holder 46 to which a cable 48 similar to the cable of 30 of FIG. 1 is electrically connected. A hollow needle 50 is mounted in the needle holder 46. The sharp pointed needle 50 can be covered between uses by a protective cap shown at 52. The cable 48 is terminated in a male cable connector 54, shown in cross-section in FIG. 3. The male connector 54 is a conventional component that allows a unipolar connection to be made to another cable by way of a matching female connector, and contains a bare wire 56 which is connected to a wire core (not shown) of the cable 48.

FIG. 4 shows how the cable 48 can be electrically connected to the metal needle 50. A metal core piece 58 to which the needle 50 is permanently connected is provided. The end of the cable 48 is stripped and the bare wire end 60 inserted into a crevice next to and in contact with the side of the bare needle 50. The metal core piece 58 is then crimped permanently connecting the bare wire end to the needle in a good electrical connection. The crimped core piece 58 with attached cable 48 is then embedded in the electrically-insulating needle holder 46. As will be observed, mounting of the electrical cable 48 to the syringe needle 50 in no way interferes with the operation of the syringe. A plunger (not shown) can be inserted in the barrel 20 of the syringe (FIG. 2) when attached to the needle holder 46. FIG. 4 also shows the needle bore 51 which extends from the tip to the hub interior. Also shown in exaggerated thickness is an electrically-insulating coating 53, for example, of Teflon, which surrounds and electrically-insulates the projecting part of the needle body 50 but leaves the tip 55 exposed so when electrosurgical currents are applied to the needle by way of the cable 48, the electrosurgical currents will be applied by way of the bare tip 55 to the patient's tissue.

In the embodiment of FIGS. 5–7, a modified connector 54 is shown which functions the same as the connector 54 in the FIG. 2 embodiment. In the FIG. 5 embodiment, the syringe barrel is inserted in the cavity 64 of the needle holder or hub 66. As before, the needle is secured as by crimping in a metal core piece 68, and the cable 48 is mounted in the electrically-insulating part of the needle holder 66 by way of a metal coupling 70 from which a bare wire extends to a second metal coupling 72 mounted on the needle 50 and which can be electrically connected thereto as by crimping or by welding or any other convenient means.

The operation is graphically depicted in FIG. 1. The hypodermic needle 26 is inserted into the vein 12 to be treated and the plunger 22 withdrawn to see whether blood is back drawn into the syringe barrel 20. If blood is detected, then the practitioner simply activates 40 the electrosurgical apparatus 38 and the resultant application of the RF electrosurgical currents via the bare needle tip quickly collapses the vein. As will be evident, the needle need not be withdrawn after the blood is detected, with the result that no problem arises of trying to locate a pin hole previously produced by a needle. As will be appreciated, once the needle is placed into the skin and the vein located, blood is drawn to confirm vein location; this is accomplished without RF power being applied. The new needle design can also be Teflon insulated. Once the vein is identified, the needle stays in the vein and the second step is to now apply RF energy to the needle via the connector end 32 going directly to the active terminal on the electrosurgical apparatus 38.

As an example only, and not meant to be limiting, the electrosurgical apparatus can be model AAOP Surgitron FFPF available from Ellman International. The Ellman equipment is preferred due to its high operating frequency exceeding 3 MHz, typically at 3.84 MHz. Also connected to the latter is the usual indifferent plate (not shown) which during use is in contact with the patient's body. A preferred needle size is 28 or 30 gauge, approximately 0.014 and 0.012 inches in diameter, respectively, though smaller gauges may be suitable for larger veins. The needle length indicated by the dimension E can vary between about ⅜ inches for the small needles to about 1¼ inches for the larger needles. The active tip portion 55 preferably has a length in the axial direction of about 0.1 inches, and can range from about 0.08–0.2 inches in length.

The thickness of the Teflon preferably is in the range of 0.0007 to 0.0013 inches. The insulation 53 must be thin because the needle 50 with the insulation 53 will be inserted into the vein to be treated.

The surgical procedure after the electrosurgical currents are applied is essentially the same as described in the referenced Patent. The insulating coating 53 is essential to prevent accidental burning or other tissue damage by the sides of the electrode as the needle is manipulated through the vein passageway.

With the Ellman equipment, the fully rectified current is used at a power setting of about 1–2 with the active bare tip electrode 50. There is very little trauma and pain felt by the patient.

It will also be understood that the electrode of the invention is not limited to its use for varicose veins. To those skilled in this art, there will certainly be other uses for this novel hypodermic needle electrode that provides an active sharpened tip connected to a hypodermic syringe, with the adjacent electrode sections coated with insulating material for accurately guiding and controlling the position of the active tip during a tissue treating electrosurgical procedure. One such possible use is to inject into the vein or other tissue a substance, such as a salt, that reacts more strongly to electrosurgical currents than the vein or tissue itself. This ensures that the electrosurgical effects are concentrated where the substance has been injected and has a lesser effect on surrounding tissue.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A surgical procedure for treating varicose veins of a patient, comprising the steps:
   (a) providing electrosurgical apparatus capable of supplying electrosurgical currents and a syringe,
     (i) the syringe comprising at one end a needle having a bore and at an opposite end means for providing suction,
     (ii) the needle terminating at one end in an active, electrically-conductive tip and with its bore accessible at the opposite end, said active tip being a sharpened point exposed electrically for applying electrosurgical currents when said needle is connected to a source of electrosurgical currents,
     (iii) portions of said needle adjacent said exposed tip being electrically-insulating to prevent contact and passage of electrosurgical currents to adjacent or surrounding tissues,
     (iv) the syringe means for providing suction being operable on the needle bore accessible at the opposite end,
     (v) said needle being configured to allow a physician to advance the exposed needle tip proximally into a vein to be treated of a patient,
   (b) advancing the electrode proximally into the vein to be treated of a patient,
   (c) providing suction at the needle bore to withdraw blood if any from the vein,
   (c) connecting the needle to the electrosurgical apparatus,
   (d) upon blood being detected, without withdrawing the needle from the vein, activating the electrosurgical apparatus to apply electrosurgical currents until the vein lining adjacent the active tip is damaged.

2. A procedure for treating varicose veins of a patient as claimed in claim 1, wherein the syringe provided in step (a) further comprises a barrel, a plunger engaging the barrel, and only a single needle.

3. A procedure for treating varicose veins of a patient as claimed in claim 1, Wherein the active tip of the needle of the syringe provided in step (a) has a length between about 0.08–0.2 inches.

4. A procedure for treating varicose veins of a patient as claimed in claim 1, wherein the sharpened point of the active tip of the needle provided in step (a) is constituted of a 28–30 gauge needle.

5. A procedure for treating varicose veins of a patient as claimed in claim 1, wherein the needle of the syringe provided in step (a) has a length of about 3/8–1 1/4 inches.

6. A procedure for treating varicose veins of a patient as claimed in claim 1, wherein the electrosurgical currents supplied by the electrosurgical apparatus provided in step (a) are at a frequency exceeding 3 MHz.

* * * * *